US 9,845,894 B2

(12) United States Patent
Olovsson

(10) Patent No.: US 9,845,894 B2
(45) Date of Patent: Dec. 19, 2017

(54) CLEANING OF ROTARY VALVES

(71) Applicant: GE Healthcare Bio-Sciences AB, Uppsala (SE)

(72) Inventor: Bjorn Olovsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 15/031,927

(22) PCT Filed: Oct. 8, 2014

(86) PCT No.: PCT/EP2014/071583
§ 371 (c)(1),
(2) Date: Apr. 25, 2016

(87) PCT Pub. No.: WO2015/062830
PCT Pub. Date: May 7, 2015

(65) Prior Publication Data
US 2016/0273664 A1 Sep. 22, 2016

(30) Foreign Application Priority Data

Oct. 31, 2013 (GB) .................................. 1319276.0

(51) Int. Cl.
*F16K 11/074* (2006.01)
*F16K 31/04* (2006.01)
*G01N 30/00* (2006.01)

(52) U.S. Cl.
CPC ........ *F16K 11/0743* (2013.01); *F16K 31/041* (2013.01); *G01N 30/00* (2013.01)

(58) Field of Classification Search
CPC ...... F16K 11/0743; F16K 31/041; F16K 1/24; G01N 30/00; Y10T 137/86549
See application file for complete search history.

(56) References Cited

U.S. PATENT DOCUMENTS 2,610,511 A 9/1952 Mansen
2,633,325 A * 3/1953 Whitlock, Jr. ............ F16K 3/10
137/625.31

(Continued)

FOREIGN PATENT DOCUMENTS

AT 309936 B 9/1973
AU 471336 B2 4/1976

(Continued)

OTHER PUBLICATIONS

International Search Report and Written Opinion regarding International Application No. PCT/EP2014/071583, dated Jan. 26, 2015, 14 pages.
Great Britain Search Report regarding GB application No. 1319276.0, dated Jan. 8, 2014, 3 pages.

*Primary Examiner* — Craig Schneider
*Assistant Examiner* — Kevin Barss
(74) *Attorney, Agent, or Firm* — Wood IP LLC

(57) ABSTRACT

Disclosed is a rotary valve 1 comprising a stator 20 and a rotor 40 generally in rotary sliding engagement with the said stator about a valve axis RA, the stator including a plurality of fluid ports 22, 26, 28, the rotor 40 being operable to selectively fluidically interconnect two or more of said ports during its rotary sliding engagement. The valve further includes an actuator (70) for disengagement of the rotor from the stator to enable efficient cleaning of the valve interconnections.

9 Claims, 4 Drawing Sheets

(56) References Cited

U.S. PATENT DOCUMENTS

| | | | | |
|---|---|---|---|---|
| 2,857,929 | A * | 10/1958 | Whitlock, Jr. | F16K 11/0743 137/375 |
| 4,540,015 | A * | 9/1985 | Henriksen | F16K 11/074 134/166 C |
| 5,295,520 | A * | 3/1994 | Acker | B67C 3/262 137/625.46 |
| 5,419,208 | A * | 5/1995 | Schick | F16K 11/085 137/625.17 |
| 5,803,117 | A * | 9/1998 | Olsen | F16K 11/0743 137/625.11 |
| 6,012,487 | A * | 1/2000 | Hauck | F16K 11/0743 137/625.11 |
| 8,286,663 | B2 * | 10/2012 | Kallback | F16K 11/0743 137/625.15 |
| 8,322,374 | B2 * | 12/2012 | Tomita | G01N 30/20 137/625.11 |
| 8,567,441 | B2 * | 10/2013 | Maeda | F16K 11/074 137/240 |
| 9,194,846 | B2 * | 11/2015 | Yasunaga | G01N 30/24 |
| 2012/0145937 | A1 * | 6/2012 | Richman | F16K 11/076 251/304 |
| 2015/0090345 | A1 * | 4/2015 | Olovsson | F16K 11/0743 137/15.06 |

FOREIGN PATENT DOCUMENTS

| | | |
|---|---|---|
| GB | 1167763 A | 10/1969 |
| WO | 2013/160455 A1 | 4/2013 |

\* cited by examiner

CLEANING OF ROTARY VALVES

CROSS-REFERENCE TO RELATED APPLICATIONS

This application is a filing under 35 U.S.C. 371 of international application number PCT/EP2014/071583, filed Oct. 8, 2014, which claims priority to Great Britain application number 1319276.0, filed Oct. 31, 2013, the entire disclosures of each of which are hereby incorporated by reference.

FIELD OF THE INVENTION

The present invention relates to the cleaning of rotary valves of the type that control fluid flow, particularly, but not exclusively, fluid flow in laboratory or bio-processing equipment such as chromatographic equipment, and more specifically to valves for directing fluid flow along a desired path, selected from a set of such paths.

BACKGROUND OF THE INVENTION

Rotary valves are commonly used in devices for controlling fluid flow. A typical type of valve, for example used in laboratory equipment of moderate sizes such as a liquid chromatography system (LCS), is a rotary selection valve employed to select an appropriate fluid path from a number of paths and thus to redirect fluid from one fluid path to another fluid path.

Generally, a rotary valve has a stationary body, herein called a stator, which co-operates with a rotating body, herein called a rotor.

In commercially available LCS rotary valves, the stator is provided with a number of inlet and outlet ports. The ports are in fluid communication with a corresponding set of orifices on an inner stator face, via bores in the stator. The inner stator face is an inner surface of the stator that is in generally fluid tight abutment with an inner rotor face of the rotor. The rotor is typically formed as a disc and the inner rotor face is pressed against the inner stator face in rotating co-operation. The inner rotor face is provided with one or more grooves which interconnect different stator orifices depending on the rotary position of the rotor with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotator or the stator reflects the intended use of a specific rotary valve.

A common type of multi-purpose valve has one inlet port (typically placed in the rotary axis of the valve) and a number of outlet ports that are placed around the inlet port. The rotor has a single, radially extending groove that has one end in the rotary axis, thereby always in fluid communication with the inlet, while the other end can be in fluid communication with any one of the outlets depending on the angular position of the rotor with respect to the stator. Such a valve is useful to direct a flow from the inlet to any of the outlets, one at a time. Other arrangements of fluid paths are known also.

Whilst these valves function very well, small amounts of leakage are possible between the abutting rotor and stator faces, which manifests itself as growths of bacteria and other microorganisms, usually around the orifices on the stator where the leakage has taken place. This in turn leads to contamination in the fluid paths as the rotor moves between selected angular positions. For highly sensitive laboratory equipment, this contamination is not acceptable, and so the valve has to be dismantled and cleaned regularly, which takes time and renders the equipment inoperable during cleaning.

One attempt to address the above issue is described in, as yet unpublished, application PCT/EP2013/058752, which provides improved rotary selection valve that requires less cleaning and is thus more convenient to use. That invention consists in a rotary selection valve, the valve comprising a stator and a rotor, said stator and rotor each having complementary abutment surfaces for allowing generally fluid tight relative rotation between the stator and the rotor about a rotational axis, said stator or rotor comprising at least one connection port in fluid communication with an associated orifice at said stator or rotor abutment surface, that invention being characterised in that said stator and/or said rotor further comprises a fluid recess extending radially beyond said associated orifice or orifices and open to the complementary abutment surfaces.

Thereby, the inventor observed that arrangement allows easier cleaning or sanitisation of the valve, because bacteria or other microorganisms cannot pass radially beyond the fluid recesses described above. The valve can be cleaned by automated means and need not be dismantled so frequently.

However the same inventor has realised that an even better system is possible which cleans the whole internal valve assembly including the complementary abutment faces mentioned above, which system can be readily automated. Embodiments of the present invention address this realisation.

The invention provides rotary valve according to claim 1 having preferred features defined by claims dependent on claim 1. The invention provides also a method as defined by claim 9 having preferred features define in subsequent claims.

BRIEF DESCRIPTION OF THE DRAWINGS

The invention can be put into effect in numerous ways, illustrative embodiments of which are described below with reference to the drawings, wherein.

DETAILED DESCRIPTION OF THE INVENTION

Figure 1:
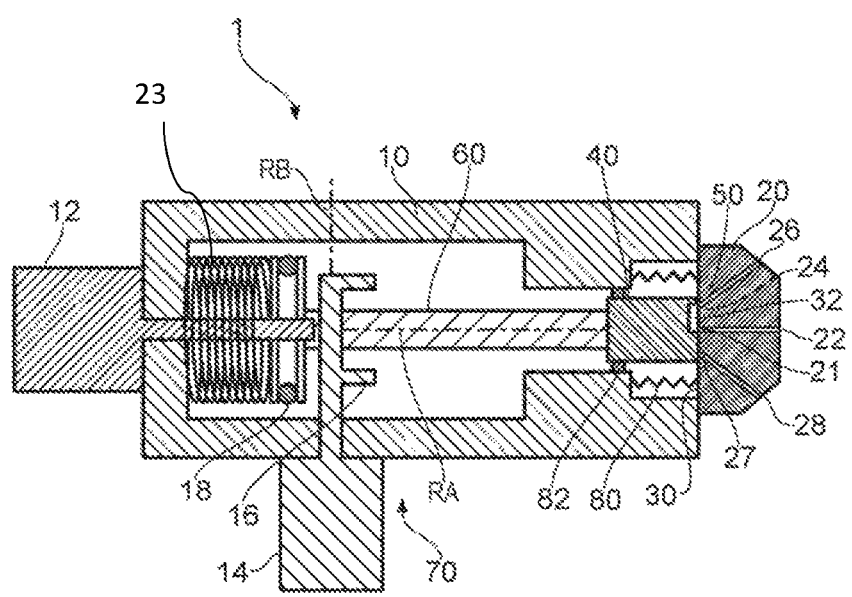
FIG. 1 shows a sectional view of part of a first rotary valve.

Referring to FIG. 1, a rotary valve 1 is illustrated schematically, showing only the main parts. The valve 1 includes a housing 10, a stator 20, a rotor 40 and a drive shaft 60, for connection to an electric motor 12, for example the d.c. motor shown or a stepper motor or other rotary drive (not shown). The drive will in practice include a means (not shown) for recognizing the angular position of the rotor. Manual operation of the valve is possible also. The rotor 40 is rotatable with respect to the stator 20 about a rotary axis RA of the valve, as a result of the rotary motion of the motor 12 and drive shaft 60.

The stator 20 is fixed with respect to the housing 10 and is provided with ports 22, 26 and 28. Ports 22, 26 and 28 are visible in FIG. 1 but more than three ports will generally be provided. The ports allow selective fluid communication between a source and any components with which the valve is to co-operate. The ports may be situated on any suitable position on the exterior surface of the stator. The ports are provided with means to connect capillaries or tubing, such as threaded recesses. Other connections are known in the art. Via fluid communication channels, the ports 22, 26 and 28 are in fluid communication with a corresponding set of orifices 21, 24 and 27 on the end face 30 of the stator 20, i.e. the surface of the stator 20 that during operation engages with the rotor 40.

The rotor 40 is typically formed as a disc and has a rotor end face 50, i.e. the surface pressed against the inner stator face 30 during operation. The faces 30 and 50 are complementary such that they provide generally fluid tight engagement. Most conveniently these faces are flat, but other complementary shapes are possible, for example they may be matched part-spherical or conical shapes. The inner rotor face 30 too is provided with one or more fluid communication channels, in the present case form of a groove 32 in the end face 30.

In use the rotor 40 can be rotated about axis RA by means of the motor 12 and shaft 60 such that the orifice 21 which remains always in communication with the groove 32, is selectively caused to communicate with either orifice 24 or orifice 27, or, in practice other circumferentially arranged orifices not shown. Thus various stator outlet ports can be made to communicate selectively with the central inlet port 22.

The foregoing detailed description describes elements of a rotary valve which are generally conventional. However, with additional reference to FIG. 2, the valve of the present invention includes an actuator 70, the function of which is disengage the rotor 40 from the stator 20, by moving the rotor 20 with linear movement away from the stator 20 towards the left when looking at FIG. 1, and thereby to provide a washing cavity 90 which allows washing fluid, typically sodium hydroxide, to circulate over the entire surfaces 30 and 50, and in turn to clean those faces and the respective orifices 21, 24 and 27. To prevent excess volumes of cleaning fluid being used, a cylindrical bellows seal 80 is connected between the stator 20 and the housing 10, and circumstances orifices 21, 24 and 27. An additional O ring seal 82 is provided between the rotor 40 and the housing 10 to prevent cleaning fluid from passing beyond the rotor 40 toward the motor 12.

In more detail the actuator 70 comprises an actuator motor 14 (for example another d.c. motor or stepper motor) and a cam 16. The cam 16 rotates 180 degrees about an axis RB which is generally perpendicular to the axis RA, in order to act upon a thrust bearing 18 attached to the shaft 60 at its radially inner region, which in turn causes said linear movement of the shaft 60 and rotor 40 from the position shown in FIG. 1 to the position shown in FIG. 2. Cleaning fluid is then pumped through the cavity 90 via port 28 in this case. When cleaning complete, the motor 14 is driving a further 180 degrees, a return spring 23 forces the shaft 60 and thereby the rotor 40 back into engagement with the stator 20, typically with a force of 1000-1500N.

Figure 2:
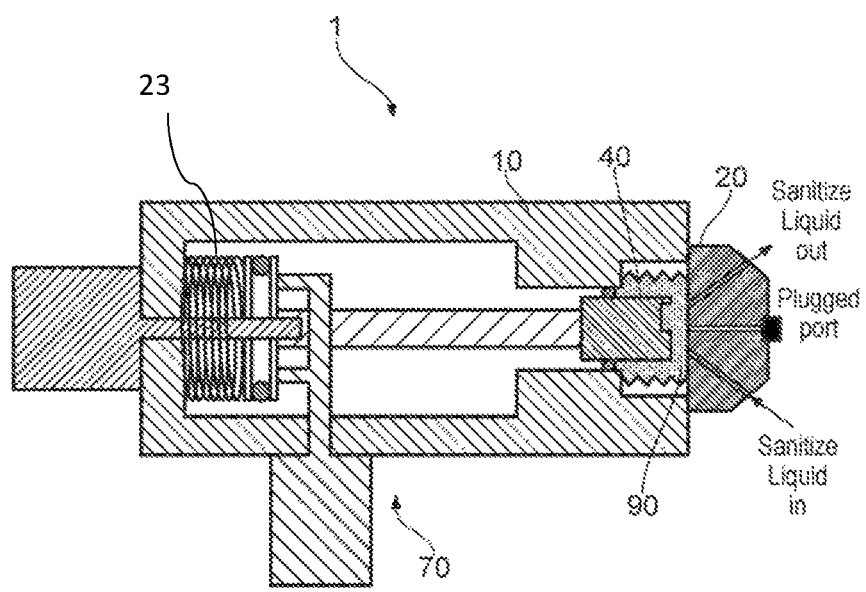
FIG. 2 shows a sectional view of the valve shown in FIG. 1, but in a different orientation.
Figure 3:
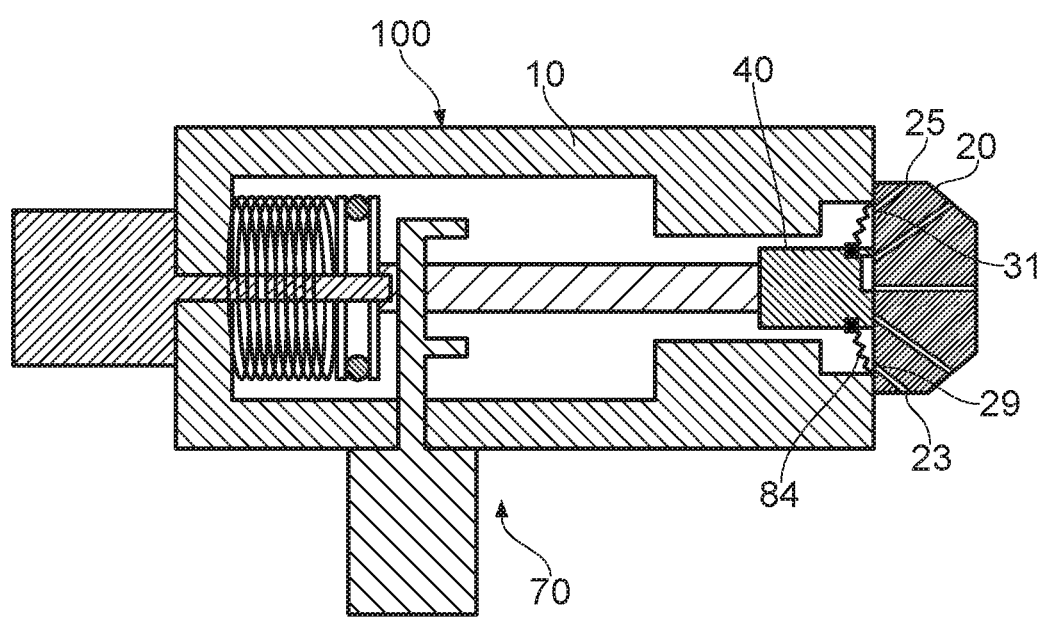
FIG. 3 shows a sectional view of part of a second rotary valve.
Figure 4:
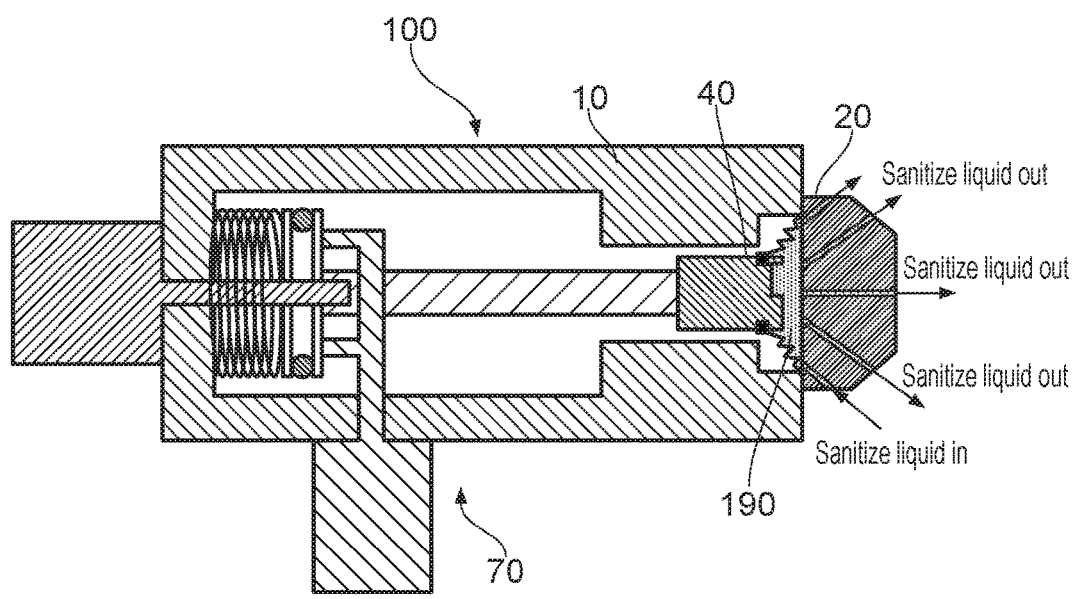
FIG. 4 shows a sectional view of the valve shown in FIG. 3, but in a different orientation.

FIGS. 3 and 4 show a valve 100 similar to that shown in FIGS. 1 and 2, with the differences described below.

In this instance the bellows seal 80 and O ring seal 82 are replaced by a single conical bellows seal 84 which at its radially outer region is compressed between the stator 20 and the housing 10, and at its radially inner region provides a rotatable seal around the rotor 40. Further the stator 20 includes a dedicated cleaning fluid inlet port 23 and outlet port 25 which in this instance are not part of the selective interconnections of the remaining valve ports.

The valve 100 operates in the same manner as valve 10, although the volume of cleaning fluid required is less. The actuator 70 again moves the rotor to the left in the drawing, as shown in FIG. 4 to produce a cleaning cavity 190. It will be noted that the inlet port 23 has a respective orifice 29 at the inner stator face which is close to the lowermost extent of the cleaning cavity 190, to act as drain for any trapped cleaning fluid. As can be seen best in FIG. 3, the inlet orifice 29 and an outlet orifice 31 associated with the outlet port 26 are located radially outside the area which the rotor engages. This means that the port 23 is in fluid communication with the port 25 even when the rotor and stator are engaged. Further, this means that a supply of cleaning fluid can be pumped through the ports when the valve is operating in its conventional fluid path switch mode. This cleansing during normal operation of the valve can be useful in preventing growth of microorganisms, for example in extended operations of the valve and its associated equipment.

It will be evident that both valves (1, 100) can be operated to provide automatic cleansing, for example at the end of operations and initiated automatically by a control signal, or can be manually selectively operated to be cleaned. There is no need to disassemble the valves and a convenient but efficient cleansing cycle can be achieved with this arrangement.

Although two embodiments have been described and illustrated, it will be apparent to the skilled addressee that additions, omissions and modifications are possible to those embodiments without departing from the scope of the invention claimed. For example, the actuator 70 shown could be modified, such that the motor 12 withdraws the rotor during a portion of its rotation, for example by using a cam rotatable about the axis RA which acts on a follower in the housing, only duration said portion of its rotation. Other arrangements are possible, for example in which the stator moves away from the rotor, or in which both the rotor and the stator move to achieve disengagement.

Whilst 3, and 5 port stators have been illustrated, it will be apparent that other numbers of ports could be employed. Although a bellows seal has been used, any flexible seal will suffice, or the seal could be omitted if the volume of cleaning fluid used is not important.

The invention claimed is:

1. A rotary valve, the valve comprising a stator and a rotor generally in rotary sliding engagement with the said stator about a valve axis (RA), the stator including a plurality of fluid ports, the rotor being operable to selectively fluidically interconnect two or more of said ports during its rotary sliding engagement, the valve being characterized in that it includes an actuator for disengaging the rotor and the stator, wherein the actuator includes a mechanism comprising an electric motor, a cam driveable by said motor and a return spring, and the mechanism is configured to move the rotor along the valve axis away from the stator, while the stator remains stationary.

2. A rotary valve as claimed in claim 1, wherein the cam is rotatable by the motor to move a drive shaft of a rotor away from the stator, and the rotor is urged to return to its engaging position by means of the return spring acting on the drive shaft.

3. A rotary valve as claimed in claim 2, wherein the motor has a rotational axis which is substantially perpendicular to the valve axis.

4. A rotary valve as claimed in claim 1, wherein the stator and rotor each include a complementary engagement face, wherein said stator face includes a plurality of orifices each in fluid communication with a respective port, and at least one fluid seal is provided which circumscribes said orifices and performs a sealing function at least when the rotor and stator are disengaged.

5. A rotary valve as claimed in claim 4, wherein the stator includes an cleaning fluid inlet for introducing cleaning fluid into a cavity formed between the disengaged stator and rotor and the seal.

6. A rotary valve as claimed in claim 5, wherein stator further includes a cleaning fluid outlet for exhausting cleaning fluid, said inlet and outlet being in fluid communication when the rotor and stator disengaged, and when they are engaged.

7. A method of cleansing a rotary valve, said valve comprising a stator and a rotor generally in rotary sliding engagement with the said stator about a valve axis (RA), the stator including a plurality of fluid ports, the rotor being operable to selectively fluidically interconnect two or more of said ports during its rotary sliding engagement, the method including the steps of:
   a) operating an actuator to disengage the rotor and the stator and thereby provide a cavity therebetween;
   b) introducing cleaning fluid into the cavity; and
   c) reengaging the rotor and stator once cleaning has taken place.

8. The method of claim 7 wherein the step of introducing cleaning fluid includes introducing said fluid via a first port in the stator, and allowing that fluid to exit via one or more further ports in the stator.

9. The method of claim 8, wherein steps a), b) and c) are carried out automatically in response to a control signal.

* * * * *